US00PP13837P29

(12) United States Plant Patent
Hoff

(10) Patent No.: US PP13,837 P2
(45) Date of Patent: May 20, 2003

(54) ZANTEDESCHIA PLANT NAMED 'RED DESIRE'

(75) Inventor: Petrus M. M. Hoff, Steenbergen (NL)

(73) Assignee: License Institute Netherlands, Steenbergen (NL)

( * ) Notice: Subject to any disclaimer, the term of this patent is extended or adjusted under 35 U.S.C. 154(b) by 0 days.

(21) Appl. No.: 10/103,954

(22) Filed: Mar. 22, 2002

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Zantedeschia plant named 'Red Desire', characterized by its upright and somewhat outwardly spreading plant habit; white-colored spathes with dark pink-colored throats and dark pink-colored spadices; and freely flowering habit.

1 Drawing Sheet

BOTANICAL CLASSIFICATION/CULTIVAR DESIGNATION

*Zantedeschia aethiopica* cultivar Red Desire.

BACKGROUND OF THE INVENTION

The present invention relates to a new and distinct cultivar of Zantedeschia plant, botanically known as *Zantedeschia aethiopica*, and hereinafter referred to by the name 'Red Desire'.

The new Zantedeschia is a product of a planned breeding program conducted by the Inventor in Steenbergen, The Netherlands. The objective of the program is to create and develop new freely flowering Zantedeschia cultivars with attractive spathe color that can be used as a cut flower as well as a container plant.

The new Zantedeschia originated from a cross-pollination by the Inventor in 1995 of a *Zantedeschia aethiopica* selection identified as white, not patented, as the female, or seed, parent with the *Zantedeschia aethiopica* cultivar Marsh Mellow, not patented, as the male, or pollen, parent. The cultivar Red Desire was discovered and selected by the Inventor as a plant within the progeny of the stated cross-pollination in a controlled environment in Steenbergen, The Netherlands.

Asexual propagation of the new cultivar by rhizome divisions in Steenbergen, The Netherlands since 1997 has shown that the unique features of this new Zantedeschia plant are stable and reproduced true to type in successive generations of asexual propagation.

BRIEF SUMMARY OF THE INVENTION

The new Zantedeschia has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Red Desire. These characteristics in combination distinguish 'Red Desire' as a new and distinct cultivar:

1. Upright and somewhat outwardly spreading plant habit.

2. White-colored spathes with dark pink-colored throats and dark pink-colored spadices.

3. Freely flowering habit.

Plants of the new Zantedeschia are most similar to plants of the parent plants. In side-by-side comparisons conducted in Steenbergen, The Netherlands, plants of the new Zantedeschia differed from plants of the female parent:

1. Plants of the new Zantedeschia were smaller than plants of the female parent.

2. Plants of the new Zantedeschia had white-colored spathes with dark pink-colored throats whereas plants of the female parent had solid white-colored spathes.

3. Plants of the new Zantedeschia had dark pink-colored spadices whereas plants of the female parent had yellow-colored spadices.

In side-by-side comparisons conducted in Steenbergen, The Netherlands, plants of the new Zantedeschia differed from plants of the male parent, the cultivar Marsh Mellow, in the following characteristics:

1. Plants of the new Zantedeschia were more freely flowering than plants of the cultivar Marsh Mellow.

2. Plants of the new Zantedeschia had white-colored spathes with dark pink-colored throats whereas plants of the cultivar Marsh Mellow had white-colored spathes with light pink-colored throats.

3. Plants of the new Zantedeschia had dark pink-colored spadices whereas plants of the cultivar Marsh Mellow had light pink to white-colored spadices.

BRIEF DESCRIPTION OF THE PHOTOGRAPH

The accompanying colored photograph illustrates the appearance of the new Zantedeschia, showing the colors as true as it is reasonably possible to obtain in colored reproductions of this type. Colors in the photograph differ slightly from the color values cited in the detailed botanical description which accurately describe the colors of the new Zantedeschia. The photograph is a close-up view of a typical inflorescence and leaves of 'Red Desire'.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe two-year old plants grown in Steenbergen, The Netherlands, in ground beds in a glass greenhouse without supplemental heat. During the production of the plants, day temperatures ranged from 2 to 22° C. and night temperatures ranged from −3 to 18° C. Light levels averaged 15,000 klux. The photographs and description were taken during the spring and summer.

Botanical classification: *Zantedeschia aethiopica* cultivar Red Desire.

Commercial classification/usage: Cut flower Calla Lily or container Calla Lily plant.

Parentage:

*Female parent.*—*Zantedeschia aethiopica* selection identified as white, not patented.

*Male parent.*—*Zantedeschia aethiopica* cultivar Marsh Mellow, not patented.

Propagation:

*Method.*—By rhizome divisions.

*Time to initiate roots.*—Summer: About 30 days at 20° C. Winter: About 60 days at 5° C.

*Time to develop roots.*—Summer: About 60 days at 20° C. Winter: About 90 days at 5° C.

*Root description.*—Strong fleshy roots; white in color.

*Rooting habit.*—Freely branching.

Plant description:

*Plant shape.*—Upright and somewhat spreading plant habit; inverted triangle, symmetrical.

*Plant height, to top of foliar plane.*—About 80 cm.

*Plant diameter or spread.*—About 80 cm.

*Foliage description.*—Quantity per plant: About 100. Length: About 20 to 30 cm. Width: About 10 to 20 cm. Shape: Ovate. Apex: Acute. Base: Cordate. Margin: Entire. Texture, upper and lower surfaces: Smooth, glabrous. Venation pattern: Pinnate. Color: Young leaves, upper surface: 144A to 144B. Young leaves, lower surface: 144B to 144C. Fully expanded leaves, upper surface: Darker than 144A to 143B. Fully expanded leaves, lower surface: 144A to 144B. Venation, upper surface: 145B. Venation, lower surface: 144A to 146A. Petiole: Length: About 80 cm. Diameter: About 2 to 4 cm. Color: 144A to 144B.

Inflorescence description:

*Inflorescence arrangement.*—Spathes with spadices arising from leaf axils at the base of the plant. Spathes upright.

*Natural flowering season.*—Plants flower in the greenhouses during June to July and outside the greenhouse from July to August in The Netherlands. Inflorescences persistent.

*Quantity of inflorescences.*—Freely flowering, typically plants develop about 20 inflorescences during the flowering season.

*Inflorescence longevity.*—Inflorescences last about 7 to 21 days on the plant and about 7 to 14 days as a cut flower.

*Fragrance.*—None detected.

*Inflorescence buds.*—Length: About 8 to 12 cm. Diameter: About 1 to 2 cm. Shape: Columnar. Color: 145C to 157C.

*Spathe.*—Length: About 12 to 18 cm. Width: About 10 to 14 cm. Shape: Broadly cordate. Apex: Cirrhous. Base: Cordate, basal lobes overlapping. Margin: Entire. Texture, upper and lower surfaces: Leathery; glabrous and smooth. Color: When opening, upper surface: 157B; towards base, 39A to 39C. When opening, lower surface: 157B; towards base, 39D. Fully opened, upper surface: 157A; towards base, 39A to 39C. Fully opened, lower surface: 157A; towards base, 39B to 39D. Venation, upper surface: 156D to 157A; towards base, 43A to 49A. Venation, lower surface: 156D to 157A; towards base, 39A.

*Spadix.*—Length: About 7 to 10 cm. Diameter: About 7 to 10 mm. Shape: Columnar. Cross section: Rounded. Longitudinal axis: Erect. Color: 43A to 43C.

*Flowers.*—Quantity per spadix: Numerous, about 200. Shape: Rounded. Diameter, female flowers: About 2 to 4 mm. Diameter, male flowers: About 1 to 2 mm.

*Reproductive organs.*—Androecium: Pollen amount: Abundant. Pollen color: 9A to 9C. Gynoecium: Pistil length: About 1 to 2 mm. Stigma shape: Rounded. Stigma color: 18D to 158A. Ovary color: 43A to 43C.

*Scape.*—Length: About 80 cm. Diameter, at base: About 1.8 to 3 cm. Diameter, towards apex: About 1.2 to 1.8 cm. Aspect: Strong and erect. Color: 144A to 144C.

*Fruit.*—Quantity per inflorescence: One. Length: About 8 to 12 cm. Diameter: About 3 to 5 cm. Texture: Leathery, smooth. Color: 14B to 14C.

*Seed.*—Quantity per fruit: About 50 to 150. Length: About 8 to 12 mm. Diameter: About 8 to 12 mm. Texture: Leathery, smooth. Color: 14B to 14C.

Disease/pest resistance: Under commercial conditions, plants of the new Zantedeschia have not been observed to be resistant to pathogens or pests common to Zantedeschia.

Temperature tolerance: Rhizomes of plants of the new Zantedeschia have been observed to tolerate temperatures from −5 to 50° C. Leaves of plants of the new Zantedeschia have been observed to tolerate temperatures from 0 to 50° C.

It is claimed:

1. A new and distinct cultivar of Zantedeschia plant named 'Red Desire', as illustrated and described.

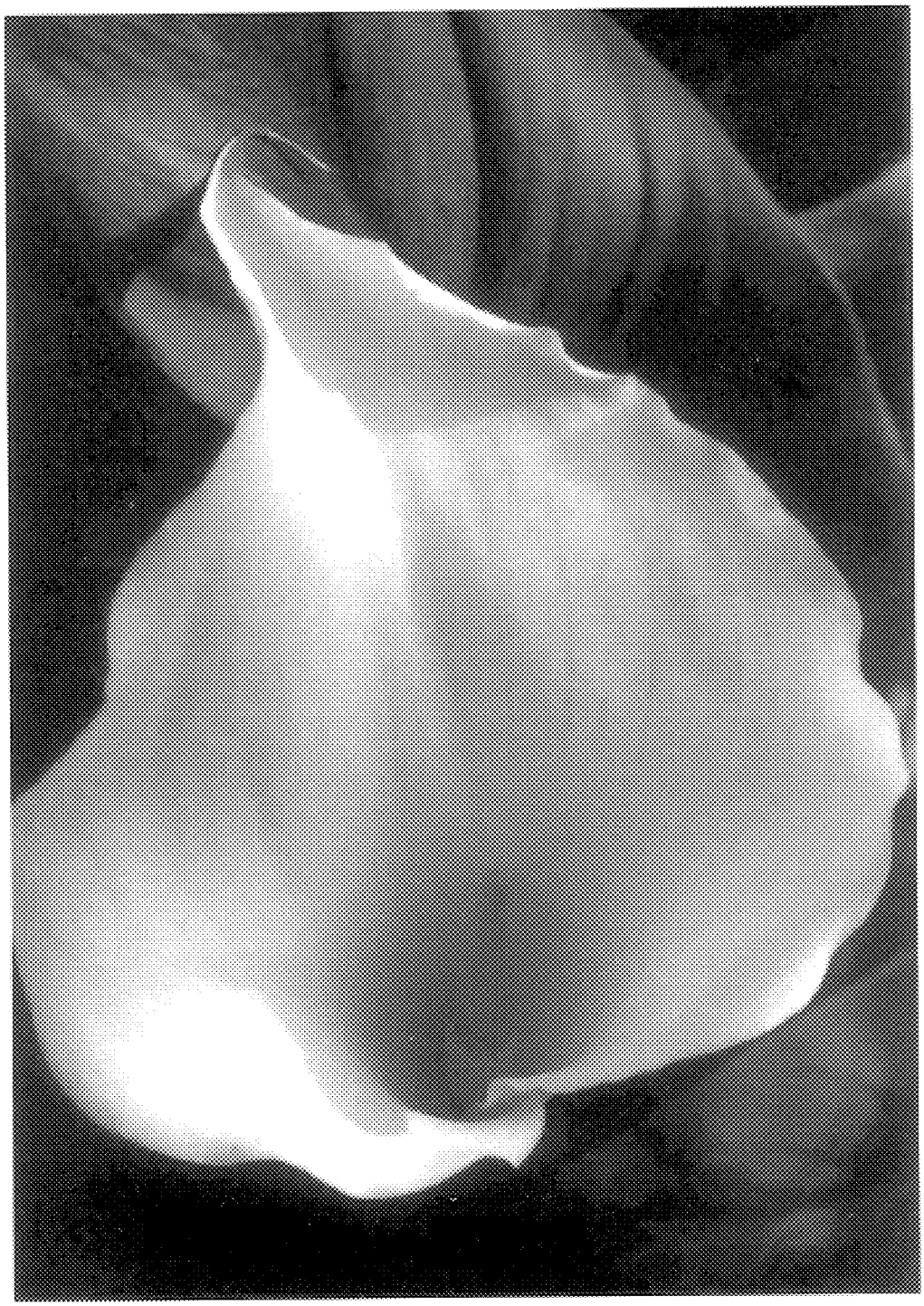

* * * * *